US012202792B2

(12) United States Patent
Dong et al.

(10) Patent No.: US 12,202,792 B2
(45) Date of Patent: Jan. 21, 2025

(54) PREPARATION METHOD FOR OPTICALLY ACTIVE CITRONELLAL

(71) Applicant: WANHUA CHEMICAL GROUP CO., LTD., Shandong (CN)

(72) Inventors: Jing Dong, Shandong (CN); Lei Yu, Shandong (CN); Yongzhen Zhang, Shandong (CN); Yuan Li, Shandong (CN)

(73) Assignee: WANHUA CHEMICAL GROUP CO., LTD., Shandong (CN)

( * ) Notice: Subject to any disclaimer, the term of this patent is extended or adjusted under 35 U.S.C. 154(b) by 470 days.

(21) Appl. No.: 17/784,015

(22) PCT Filed: Dec. 9, 2019

(86) PCT No.: PCT/CN2019/124027
§ 371 (c)(1),
(2) Date: Jun. 9, 2022

(87) PCT Pub. No.: WO2021/114021
PCT Pub. Date: Jun. 17, 2021

(65) Prior Publication Data
US 2023/0043867 A1 Feb. 9, 2023

(51) Int. Cl.
C07C 45/62 (2006.01)
B01J 31/28 (2006.01)
C07C 45/82 (2006.01)

(52) U.S. Cl.
CPC ............. *C07C 45/62* (2013.01); *B01J 31/28* (2013.01); *C07C 45/82* (2013.01); *C07B 2200/07* (2013.01)

(58) Field of Classification Search
CPC ........... C07C 45/62; C07C 45/82; B01J 31/28
See application file for complete search history.

(56) References Cited

U.S. PATENT DOCUMENTS

| 4,237,072 | A | 12/1980 | Aviron-Violet et al. | |
|---|---|---|---|---|
| 8,318,985 | B2 * | 11/2012 | Heydrich | C07C 29/56 568/830 |
| 9,988,331 | B2 * | 6/2018 | Heydrich | C07C 45/82 |
| 2013/0046118 | A1 | 2/2013 | Heydrich et al. | |
| 2013/0253228 | A1 | 9/2013 | Tsuda et al. | |

FOREIGN PATENT DOCUMENTS

| CN | 1768070 | A | 5/2006 |
|---|---|---|---|
| CN | 101039894 | A1 | 9/2007 |
| CN | 101675020 | A | 3/2010 |
| CN | 101932543 | A | 12/2010 |
| CN | 103249484 | A | 8/2013 |
| CN | 105330557 | A | 2/2016 |
| CN | 107250091 | A | 10/2017 |
| CN | 109071578 | A | 12/2018 |
| WO | WO 2004094442 | A2 | 11/2004 |
| WO | WO 2008132057 | A1 | 11/2008 |
| WO | WO 2017191310 | A1 | 11/2017 |

OTHER PUBLICATIONS

C. Jakel, et al., "The Asymmetric Hydrogenation of Enones—Access to a New L-Menthol Synthesis", Asymmetric Catalysis on Industrial Scale (2nd Edition), pp. 187-205, Dec. 2010.
T. Dang, et al., "Catalysis of the homogeneous-phase hydrogenation of $\alpha,\beta$-unsaturated aldehydes. Application to the asymmetric synthesis of citronellal", Journal of Molecular Catalysis, pp. 51-59, Dec. 1982.
S. Zhang, "Selective homogeneous catalytic hydrogenation of $\alpha,\beta$-unsaturated aldehydes and ketones", Nature Magazine, pp. 397-398, Dec. 1984.
Z. Xiong et al., "Stability of Catalysts", Air Pollution Control Technologies and Engineering Applications, pp. 296-302, Jul. 2003.
S. Zhang, "Selective homogeneous catalytic hydrogenation of $\alpha$, $\beta$-unsaturated aldehydes and ketones", Organic Chemistry, pp. 306-309, Dec. 1991.
C. Tian, "Catalyst deactivation and regeneration", Organic Chemical Technology, pp. 65-71, Sep. 1998.
European Search Report issued for Application No. 19955750.5, mailed Sep. 8, 2023.
Chinese Office Action with English Translation issued for Application No. 201911253435.6, mailed Feb. 17, 2022.
International Search Report dated Sep. 10, 2020 for International Application No. PCT/CN2019/124027, 6 pages.

* cited by examiner

*Primary Examiner* — Sikarl A Witherspoon
(74) *Attorney, Agent, or Firm* — Barnes & Thornburg LLP

(57) ABSTRACT

A preparation method for optically active citronellal, which can obviously enhance the catalytic stability of an optically active transition metal catalyst for asymmetric hydrogenation of homogeneous catalysis and thereby achieve higher turnover numbers. In the preparation method for optically active citronellal, a substrate is subjected to an asymmetric hydrogenation reaction in the presence of the transition metal catalyst to generate the optically active citronellal, wherein the transition metal catalyst is obtained by reacting a transition metal compound with an optically active ligand containing two phosphorus atoms, and the raw material of the substrate is one of neral and geranial or a combination thereof to control the hydroxyl value to be less than or equal to 6 mgKOH/g and/or the iron content to be less than or equal to 50 ppm in the raw material of the substrate for the asymmetric hydrogenation reaction.

19 Claims, No Drawings

PREPARATION METHOD FOR OPTICALLY ACTIVE CITRONELLAL

TECHNICAL FIELD

The present disclosure relates to a preparation method for optically active citronellal, specifically to a method for preparing optically active citronellal, in particular R-citronellal, by asymmetric hydrogenation of neral and/or geranial.

BACKGROUND

Citronellal is an important spice component, which is widely used in flavoring and preparation of beverages, candies and foods. It is also an important intermediate compound, and especially, citronellal having optical activity is an important intermediate for the synthesis of L-menthol.

EP 0000315 discloses a process for preparing optically active R-citronellal by hydrogenation of geranial or neral in the presence of a catalyst complex, wherein the catalyst complex is soluble in the reaction system and composed of rhodium and chiral phosphine.

J. Mol. Cat. 16 (1982) 51-59 and Helv. Chim. Acta. 84 (2001) 230-242 report the homogeneously catalyzed hydrogenation of α,β-unsaturated aldehydes, and use the method for preparing optically active R-citronellal. The catalyst used in this study is a complex of rhodium carbonyl and chiral phosphine.

CN 101039894 discloses a method for the production of optically active R-citronellal by means of homogeneously catalyzed hydrogenation of neral using a complex of rhodium carbonyl and chiral phosphine, where the catalyst is preformed by a mixture of CO and $H_2$, and the reaction is carried out in $H_2$ mixed with a small amount of CO.

The methods reported above have the advantages of high chemical selectivity and stereoselectivity. However, the homogeneous transition metal catalyst prepared using a transition metal compound and a chiral ligand has the disadvantage of low hydrogenation efficiency, and especially under the condition of a high molar ratio of substrate/catalyst, the catalyst conversion frequency is obviously reduced, which leads to the problem that the catalyst needs to be recycled and reused for many times. In this way, the process operation is complicated, the catalyst is prone to metal coupling deactivation, the turnover number is low, and when the catalyst is applied on an industrial scale, the cost is high.

Therefore, it is necessary to find a method for preparing optically active citronellal by asymmetric hydrogenation of neral and/or geranial, so as to achieve high turnover numbers of the catalyst, thereby reducing the cost of the catalyst to an acceptable level for industrial-scale production.

SUMMARY

The object of the present disclosure is to provide a preparation method for optically active citronellal, which can obviously enhance the catalytic stability of an optically active transition metal catalyst for homogeneously catalyzed asymmetric hydrogenation and thereby achieve higher turnover numbers.

To achieve the object, the present disclosure provides the technical solutions described below.

A preparation method for optically active citronellal, wherein a substrate is subjected to an asymmetric hydrogenation reaction in the presence of a transition metal catalyst to generate the optically active citronellal, the transition metal catalyst is obtained by reacting a transition metal compound with an optically active ligand containing two phosphorus atoms, and the substrate is selected from one or a combination of two of neral of Formula (I) and geranial of Formula (II), wherein the substrate for the asymmetric hydrogenation reaction is controlled to have a hydroxyl value less than or equal to 6 mgKOH/g and/or an iron content less than or equal to 50 ppm (ppm based on mass):

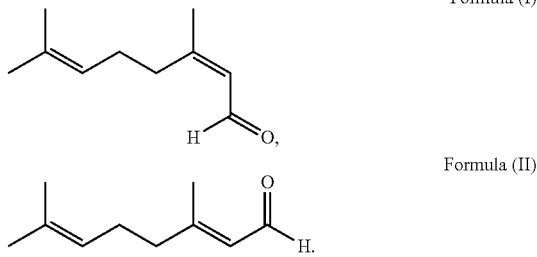

The inventors of the present application surprisingly find that the catalytic stability of an optically active transition metal catalyst for homogeneously catalyzed asymmetric hydrogenation can be significantly enhanced (the catalyst specifically refers to a catalyst obtained by reacting a transition metal compound with an optically active ligand containing two phosphorus atoms), thereby achieving higher turnover numbers, by adopting any one of the following manners to control the hydroxyl value and/or the iron content in the substrate (neral and/or geranial): by controlling the hydroxyl value in the substrate (neral and/or geranial) to be less than or equal to 6 mgKOH/g (e.g. 6 mgKOH/g, 4 mgKOH/g, 1 mgKOH/g, etc.) (in this case, the iron content is unnecessary to be considered, which, for example, may be less than or equal to 50 ppm or greater than 50 ppm); by controlling the iron content (i.e. the content of iron element) in the substrate (neral and/or geranial) to be less than or equal to 50 ppm (e.g. 50 ppm, 10 ppm, 1 ppm, etc.) (in this case, the hydroxyl value is unnecessary to be considered, which, for example, may be less than or equal to 6 mgKOH/g or greater than 6 mgKOH/g); or by simultaneously controlling the hydroxyl value to be less than or equal to 6 mgKOH/g and the iron content (i.e. the content of iron element) to be less than or equal to 50 ppm in the substrate (neral and/or geranial).

In the present disclosure, the substrate (neral and/or geranial) in which the hydroxyl value is less than or equal to 6 mgKOH/g and/or the iron content is less than or equal to 50 ppm is obtained by rectification of the substrate (neral and/or geranial), where the rectification operation is known and has been well-described in the literature (e.g. CN 101687751 B, etc.) or may be performed by those skilled in the art using process conditions similar to those known. The hydroxyl value and the iron content in neral and geranial can be controlled by controlling an appropriate reflux ratio and an appropriate production ratio of light and heavy components to neral and geranial in the rectification process (as exemplified in Examples 1 to 6 below). In some embodiments, the substrate for the asymmetric hydrogenation reaction is previously subjected to a rectification treatment to enable the hydroxyl value to be less than or equal to 6 mgKOH/g and/or the iron content to be less than or equal to 50 ppm in the substrate.

In the present disclosure, the substrate may be either neral or geranial or a mixture of neral and geranial. Preferably, the optically active citronellal is prepared by asymmetrically hydrogenation of a neral raw material in which the molar ratio of neral to geranial is at least 90:10 or a geranial raw material in which the molar ratio of geranial to neral is at least 90:10.

In the present disclosure, the optical purity of the optically active citronellal is at least 70 ee %, preferably 80 ee % to 99.9 ee %. As is known to those skilled in the art, the optical purity that can be obtained depends on the ratio of neral to geranial in the raw material, the type and purity of the chiral ligand, and for example, when the molar ratio of neral to geranial is higher than 90:10 and the purity of the chiral ligand is higher than 99%, the optical purity of the citronellal can reach 80 ee % to 99.9 ee %.

The optically active citronellal is optically active R-citronellal of Formula (III):

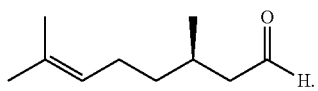

Formula (III)

The present disclosure is carried out in the presence of a transition metal catalyst obtained by reacting at least one transition metal compound soluble in the reaction mixture for the asymmetric hydrogenation reaction with an optically active ligand containing two phosphorus atoms. The catalyst may be one that is specifically disclosed in the art. In some embodiments, the molar ratio of transition metal atoms in the transition metal compound to the optically active ligand is (0.5-10):1, preferably (0.5-2):1.

In some embodiments, the optically active ligand containing two phosphorus atoms is a ligand of general formula (IV):

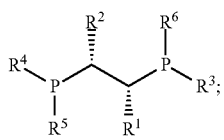

Formula (IV)

wherein
$R^1$ and $R^2$ are each independently a hydrogen atom or unbranched, branched (specifically branched alkyl of 3-20 carbon atoms) or cyclic (specifically cyclic alkyl of 3-20 carbon atoms) alkyl having 1-20 carbon atoms, and optionally carry one or more, for example, 1 to 4, ethylenic double bonds and/or optionally carry one or more, for example, 1 to 4, identical or different substituents selected from the group consisting of halogen, $C_6$-$C_{10}$ aryl and $C_3$-$C_9$ heteroaryl; or $R^1$ and $R^2$ together may form one or more 4- to 20-membered rings, where preferably the ring contains unsaturated double bonds, and ring-forming atoms on the ring are C atoms;
$R^3$, $R^4$, $R^5$ and $R^6$ are identically or differently $C_6$-$C_{10}$ aryl and each optionally carry one or more, usually 1 to 8, preferably 1 to 4, substituents selected from the group consisting of $C_1$-$C_4$ alkyl, $C_6$-$C_{10}$ aryl, $C_1$-$C_4$ alkoxy and amino.

For example, the following compounds or enantiomers thereof are preferably the optically active ligand containing two phosphorus atoms:

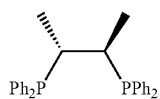

Formula (V)

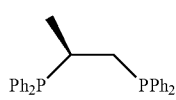

Formula (VI)

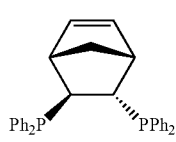

Formula (VII)

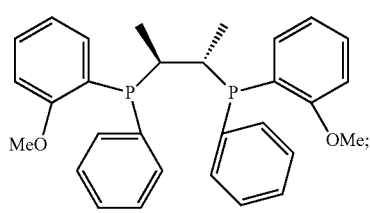

Formula (VIII)

wherein Ph refers to phenyl and $Ph_2$ refers to two phenyl groups connected to P.

In some embodiments, the transition metal compound is compounds of metals of Group VIII of the Periodic Table of Elements, in particular, one or more of compounds of Ru, Rh, Pd, Ir and Pt, and more preferably compounds of Rh.

Suitable compounds of the transition metal are in particular those soluble in the selected reaction medium (i.e. the substrate and an optional solvent), such as salts or complexes with a suitable ligand such as carbonyl, acetylacetonate, hydroxyl, cyclooctadiene, norbornadiene, cyclooctene, methoxy, acetyl or other aliphatic or aromatic carboxylate salts. Preferred transition metal compounds in the method of the present disclosure are Rh(I) and Rh(III) and Rh(0) compounds. Transition metal compounds that already have at least one CO ligand are preferred. Examples of the transition metal compounds that may be used according to the present disclosure are: $RhCl_3$, $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$ or $Rh_6(CO)_{16}$, where "acac" is an acetylacetonate ligand and "cod" is a cyclooctadiene ligand. The transition metal compounds and complexes and other examples thereof are known and have been well-described in the literature or may be prepared by those skilled in the art similarly to known compounds.

According to the present disclosure, based on the amount of the substrate to be hydrogenated (i.e. the total amount of neral and geranial), the amount of the transition metal compound is usually about 0.0001 mol % to about 0.1 mol % based on the molar amount of transition metal atoms. The catalyst can be recycled and reused by a method known to those skilled in the art. For example, after the resulting reaction product is extracted from the reaction mixture by distillation, the remaining catalyst may be used in further reaction processes. In the method of the present disclosure, the turnover number of the transition metal catalyst is greater than 50000, for example, the total turnover number of the catalyst may reach 100000-2000000.

In the present disclosure, the selection of a solvent used in the asymmetric hydrogenation reaction is not important, and preferably, the asymmetric hydrogenation reaction is carried out in the absence of a solvent.

In the present disclosure, the transition metal compound and the optically active ligand are added to the substrate to be hydrogenated, and hydrogen gas is introduced to carry out the asymmetric hydrogenation. The purity of hydrogen gas used for the asymmetric hydrogenation is 90%-100% (v/v), the impurity includes nitrogen gas, carbon monoxide, carbon dioxide and the like, and the content of impurity is 0-10% (v/v). The absolute pressure of the asymmetric hydrogenation reaction is 0.1-10 MPa, preferably 5-8 MPa; and the reaction temperature is 0-120° C., for example 25° C.-120° C., preferably 50° C.-90° C. Generally, the reaction time for the asymmetric hydrogenation of the present disclosure is about 1 hour to about 150 hours, preferably about 2 hours to about 24 hours, which is not limited thereto.

In some embodiments, the asymmetric hydrogenation reaction is carried out in the presence of hydrogen gas containing 100-10000 ppm carbon monoxide (based on volume).

In the present disclosure, the chemical selectivity of the product of asymmetric hydrogenation can reach up to 99.8%, and the conversion rate can reach up to 99.9%.

Reactors suitable for carrying out the asymmetric hydrogenation reaction of the present disclosure are in principle all vessels that allow the reaction under the conditions described above, in particular the pressure and temperature, and that are suitable for the hydrogenation reaction, such as autoclaves, tubular reactors, bubble columns, etc.

In some embodiments, the preparation method specifically includes the following steps:
dissolving the transition metal compound and the optically active ligand containing two phosphorus atoms in the substrate under an inert gas (e.g. argon) atmosphere, to obtain a mixed material containing the catalyst; before the asymmetric hydrogenation reaction is carried out, stirring the mixed material at 40° C.-80° C. (e.g. 60° C.) for 1-6 hours (e.g. 3 hours) under the condition that the volume ratio of $CO/H_2$ is ½-¾ (e.g. 1:1) and the pressure is 0.5-5 MPa (e.g. 0.8 MPa), and then cooling the mixed material to complete the pretreatment of the catalyst, so as to obtain a mixed material containing a pretreated catalyst;
subjecting the mixed material containing the pretreated catalyst to a reaction under reaction conditions required for carrying out the asymmetric hydrogenation reaction, to obtain the optically active citronellal. According to the production needs, the substrate feed can be supplemented to the reaction system. After the reaction is finished, the product can be distilled out, and the substrate can be continuously supplemented for the next round of reaction.

The technical solutions provided by the present disclosure have the following beneficial effects.

The commercial artificially synthesized neral/geranial is mostly obtained by subjecting prenol and prenal as raw materials to a condensation reaction under the action of an acidic catalyst to generate the corresponding acetal, then subjecting the acetal to a cleavage reaction under the catalysis of an acidic catalyst, and subjecting the obtained product to a rearrangement reaction. In the above process, neral/geranial is prone to intramolecular ene reaction and generates a hydroxyl-containing compound similar to Formula (IX); and in the process of cleavage and rearrangement, prenol of Formula (X) is also continuously generated. Since the acidic catalyst corrodes the material of reaction devices, neral/geranial may contain iron-containing impurities, and these impurities may easily generate carbonyl iron compounds under reaction conditions. The inventors of the present application find that when citronellal is prepared using neral and/or geranial as the substrate, where the substrate includes but is not limited to hydroxyl-containing impurities of Formula (IX) and Formula (X) and a carbonyl iron compound generated under reaction conditions, the hydroxyl-containing impurities and the carbonyl iron compound will compete with the optically active ligand in the catalyst used for preparing citronellal, then complex with the transition metal and thus destroy the structure of the catalyst, causing the gradual deactivation of the catalyst. The inventors of the present application find that by controlling the hydroxyl value and/or the iron content in the substrate neral and/or geranial, the cumulative toxicity of trace hydroxyl-containing impurities and carbonyl iron compound in the raw material to the catalyst under a high turnover number can be significantly reduced, and the catalytic stability of an optically active transition metal catalyst for homogeneously catalyzed asymmetric hydrogenation is enhanced. Therefore, in one aspect, the catalytic activity of the catalyst is significantly improved, and in another aspect, the service life of the catalyst is significantly improved, which is beneficial to the reusability of the homogeneous catalyst, thereby achieving higher turnover numbers:

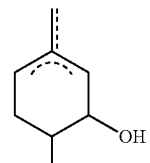

Formula (IX)

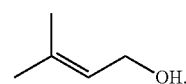

Formula (X)

The preparation method of the present disclosure can be operated batchwise, semi-continuously or continuously, and is particularly suitable for the industrial-scale production.

DETAILED DESCRIPTION

The method of the present disclosure will be further described through specific examples, but the present disclosure is not limited by the listed examples and shall comprise any other well-known variations within the scope of the claims of the present disclosure.

The pressure herein refers to the absolute pressure.

Analytical Instrument

Gas chromatograph: Agilent 7890, with chromatographic column DB-5 (for determining the conversion rate) and chromatographic column Supelco β-DEX™ 225 (for determining the optical purity), where the sample inlet temperature was 300° C.; the split ratio was 50:1; the carrier gas flow rate was 52.8 ml/min; the heating procedure was as follows: hold at 95° C. for 40 minutes, raise to 180° C. at the rate of 10° C./min, and hold for 40 minutes, and the detector temperature was 280° C.

Method for determining the hydroxyl value: Method A in GBT12008.3-2009, phthalic anhydride method.

The method for determining the iron content is described as follows:

Nitric acid: guaranteed reagent (GR);

Iron standard solution: developed by the National Research Center for Certified Reference Materials, China, with a concentration of 1000 mg/L;

Establishment of a standard curve: 12.5 mL of the iron standard solution was accurately taken into 1000 mL volumetric flask, and diluted to 1000 mL with 2% $HNO_3$ to prepare 12.5 ppm iron standard solution. 0 mL, 1.00 mL, 2.00 mL, 3.00 mL and 4.00 mL of the above 12.5 ppm iron standard solution were accurately taken and placed in five 25 mL volumetric flasks, 5 mL of 1% $HNO_3$ was added to the five volumetric flasks respectively, and the solutions were diluted to the scale mark with water and shaken well for later use; a series of standard solutions with iron concentrations of 0 ppm, 0.5 ppm, 1 ppm, 1.5 ppm and 2.0 ppm were obtained. The absorbance of the above standard solutions was determined by atomic absorption spectrophotometer AA-6300 (SHIMADZU). With the iron concentration as the ordinate and the absorbance as the abscissa, a standard curve was drawn, and the standard curve was recorded as Y=aX+b (Y: iron concentration, X: absorbance, a: slope of the standard curve, b: intercept of the standard curve).

Sample pretreatment: about 0.5 g of the raw material (accurate to 0.0001 g, denoted as $m_1$) was placed in a polytetrafluoroethylene digestion tank, 10-12 mL of nitric acid was added (slowly added to prevent violent reaction), the sealing cover was covered after the system in the digestion tank became stable, the tank was put into Atonpaar Multiwave 3000 microwave digester for digestion at a power of 1000 W for 30 minutes, the polytetrafluoroethylene digestion tank was taken out after the completion of digestion, cooled, transferred to a 25 mL volumetric flask, washed with ultrapure water three times, transferred to a volumetric flask, and shaken well to obtain a sample. At this point, the total mass of the sample was denoted as $m_2$. The absorbance $X_1$ of the above sample was determined by atomic absorption spectrophotometer, and the iron content of the sample was calculated as $(aX_1+b)*m_2/m_1$ according to the above standard curve.

Conversion rate:

Conversion rate=1-(peak area of neral in gas chromatography+peak area of geranial in gas chromatography)/total peak area in gas chromatography (except solvent)

Optical purity:

Optical purity ee %=(peak area of R-citronellal in gas chromatography-peak area of S-citronellal in gas chromatography)/(peak area of R-citronellal in gas chromatography+peak area of S-citronellal in gas chromatography)

Yield:

Yield=peak area of citronellal in gas chromatography/total peak area in gas chromatography (except solvent)

Turnover number:

Turnover number=molar amount of citronellal obtained by reaction/molar amount of rhodium in the catalyst used Reagents:

raw material (neral): 99%, J&K SCIENTIFIC;
raw material (geranial): 99%, J&K SCIENTIFIC;
$Rh(CO)_2acac$, $[Rh(cod)OH]_2$, $[Rh(cod)OMe]_2$, $Rh_4(CO)_{12}$, $Rh_6(CO)_{16}$, 98 wt %, ALDRICH;
compounds of Formula (V)-Formula (VIII) and the isomer of the compound of Formula (V) (the compound of Formula (V) was specifically (R,R)-chiraphos, the enantiomer of which was (S,S)-chiraphos), 99 wt %, J&K SCIENTIFIC.

The substrates with specific hydroxyl value and iron content in Examples 7-18 may be obtained by those skilled in the art according to existing rectification processes as described above or with reference to the rectification processes described in Examples 1-6.

Example 1 (Pretreatment of the Substrate)

The rectification column for rectifying the raw materials neral and geranial consisted of a vacuum jacketed rectification column with a length of 1 meter and an inner diameter of 50 mm, with triangular spiral packings having a diameter of 1.5 mm provided inside therein, and the separation performance of the whole column was determined to be 41 theoretical trays through separation performance determination using a mixture of cis- and trans-isomers of decahydronaphthalene (the molar ratio of cis- and trans-isomers was 1:1) at a top pressure of 1000 Pa. The column was equipped with a thin film evaporator (whose evaporation area was 0.07 $m^2$) heated by oil and a condenser cooled by cooling water.

500 g of neral with 99% purity was subjected to batch rectification at the top pressure of 1000 Pa. The heating temperature of the thin film evaporator at the bottom of the column was 100° C., and the temperature of the condenser at the top was 20° C. After total reflux for 1 hour, the equilibrium of the column was established, and the reflux ratio was adjusted to 100:1 for overhead production. After 40 g of the fore-cut fraction was produced from the overhead, a neral product collection tank was used for collection, and the rectification was stopped after 400 g was continuously produced. The hydroxyl value of neral obtained by rectification was 6 mgKOH/g and the iron content was 80 ppm.

Example 2 (Pretreatment of the Substrate)

500 g of geranial with 99% purity was subjected to batch rectification at the top pressure of 1000 Pa using the rectification column described in Example 1. The heating temperature of the thin film evaporator at the bottom of the column was 100° C., and the temperature of the condenser at the top was 20° C. After total reflux for 1 hour, the equilibrium of the column was established, and the reflux ratio was adjusted to 100:1 for overhead production. After 80 g of the fore-cut fraction was produced from the overhead, a geranial product collection tank was used for collection, and the rectification was stopped after 380 g was continuously produced. The hydroxyl value of geranial obtained by rectification was 1 mgKOH/g and the iron content was 60 ppm.

Example 3 (Pretreatment of the Substrate)

500 g of neral with 99% purity was subjected to batch rectification at the top pressure of 1000 Pa using the rectification column described in Example 1. The heating temperature of the thin film evaporator at the bottom of the column was 100° C., and the temperature of the condenser at the top was 20° C. After total reflux for 1 hour, the equilibrium of the column was established, and the reflux ratio was adjusted to 150:1 for overhead production. After 100 g of the fore-cut fraction was produced from the overhead, a neral product collection tank was used for collection, and the rectification was stopped after 350 g was continuously produced. The hydroxyl value of neral obtained by rectification was 1 mgKOH/g and the iron content was 60 ppm.

Example 4 (Pretreatment of the Substrate)

500 g of neral with 99% purity was subjected to batch rectification at the top pressure of 1000 Pa using the rectification column described in Example 1. The heating temperature of the thin film evaporator at the bottom of the column was 100° C., and the temperature of the condenser at the top was 20° C. After total reflux for 1 hour, the equilibrium of the column was established, and the reflux ratio was adjusted to 120:1 for overhead production. After 10 g of the fore-cut fraction was produced from the overhead, a neral product collection tank was used for collection, and the rectification was stopped after 250 g was continuously produced. The iron content of neral obtained by rectification was 50 ppm, and the hydroxyl value was 10 mgKOH/g.

Example 5 (Pretreatment of the Substrate)

500 g of geranial with 99% purity was subjected to batch rectification at the top pressure of 1000 Pa using the rectification column described in Example 1. The heating temperature of the thin film evaporator at the bottom of the column was 100° C., and the temperature of the condenser at the top was 20° C. After total reflux for 1 hour, the equilibrium of the column was established, and the reflux ratio was adjusted to 150:1 for overhead production. After 35 g of the fore-cut fraction was produced from the overhead, a geranial product collection tank was used for collection, and the rectification was stopped after 200 g was continuously produced. The iron content of geranial obtained by rectification was 10 ppm, and the hydroxyl value was 8 mgKOH/g.

Example 6 (Pretreatment of the Substrate)

500 g of neral with 99% purity was subjected to batch rectification at the top pressure of 1000 Pa using the rectification column described in Example 1. The heating temperature of the thin film evaporator at the bottom of the column was 100° C., and the temperature of the condenser at the top was 20° C. After total reflux for 1 hour, the equilibrium of the column was established, and the reflux ratio was adjusted to 150:1 for overhead production. After 100 g of the fore-cut fraction was produced from the overhead, a neral product collection tank was used for collection, and the rectification was stopped after 200 g was continuously produced. The iron content of neral obtained by rectification was 1 ppm, and the hydroxyl value was 8 mgKOH/g.

Example 7 (Preparation of R-Citronellal)

Under an argon gas atmosphere, 7.5 mg of $Rh(CO)_2acac$ and 18.6 mg of (R,R)-chiraphos (compound of Formula (V)) (the molar ratio was 0.66:1) were dissolved in 441.8 g of neral from Example 1 having a hydroxyl value of 6 mgKOH/g and an iron content of 80 ppm (the molar ratio of neral/geranial double bond isomers=99:1; the molar ratio of the substrate/catalyst (based on the transition metal in the catalyst)=100000), and then transferred to a 1000 mL autoclave that had been purged three times in advance with a mixture of carbon monoxide and hydrogen gas (1:1 volume/volume). The mixture was stirred for 3 hours at a 1:1 (volume/volume) $CO/H_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 60° C. and reacted for 18 hours, by using gas chromatography, the conversion rate was determined to be 99.9%, and the yield of R-citronellal with an optical purity of 88 ee % was determined to be 99%.

The turnover number based on the whole reaction of R-citronellal with $Rh(CO)_2acac$ was 99000.

Example 8 (Preparation of R-Citronellal)

Under an argon gas atmosphere, 7.5 mg of $Rh(CO)_2acac$ and 18.6 mg of (S,S)-chiraphos (the molar ratio was 0.66:1) were dissolved in 441.8 g of geranial from Example 2 having a hydroxyl value of 1 mgKOH/g and an iron content of 60 ppm (the molar ratio of geranial/neral double bond isomers=99:1; the molar ratio of the substrate/catalyst (based on the transition metal in the catalyst)=100000), and then transferred to a 1000 mL autoclave that had been purged three times in advance with a mixture of carbon monoxide and hydrogen gas (1:1 volume/volume). The mixture was stirred for 3 hours at a 1:1 (volume/volume) $CO/H_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 60° C. and reacted for 18 hours, by using gas chromatography, the conversion rate was determined to be 99.9%, and the yield of R-citronellal with an optical purity of 87 ee % was determined to be 99%.

After the product was distilled, 441.8 g of geranial having a hydroxyl value of 1 mgKOH/g and an iron content of 60 ppm (the mole ratio of geranial/neral double bond isomer=99:1) were added and stirred in an autoclave at 5 MPa synthesis gas ($H_2/CO$=1:1, volume/volume) and at 60° C. for 6 hours. The reaction pressure was adjusted to 8 MPa by injecting hydrogen gas containing 1000 ppm carbon monoxide. To reduce the CO partial pressure, the pressure was reduced to 0.5 MPa three times and restored to 5 MPa three times by injecting hydrogen gas containing 1000 ppm carbon monoxide. After the mixture was heated up to 90° C. and reacted for 24 hours, by using gas chromatography, the conversion rate was determined to be 99.9%, and the yield of R-citronellal with an optical purity of 85 ee % was determined to be 99%.

After the product was distilled again, 441.8 g of geranial having a hydroxyl value of 1 mgKOH/g and an iron content of 60 ppm (the mole ratio of geranial/neral double bond isomer=99:1) were added and stirred in an autoclave at 5 MPa synthesis gas ($H_2/CO$=1:1, volume/volume) and at 60° C. for 6 hours. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 25° C. and reacted for 48 hours, by using gas chromatography, the conversion rate was determined to be 99.9%, and the yield of R-citronellal with an optical purity of 95 ee % was determined to be 99%.

The turnover number based on the whole reaction of R-citronellal with Rh(CO)$_2$acac was 29700.

Example 9 (Preparation of R-Citronellal)

For an autoclave 1 and an autoclave 2 connected in series, in the autoclave 1 was introduced a mixture of 213 mg of Rh(CO)$_2$acac and 180 mg of (R,R)-chiraphos (compound of Formula (V)) (the molar ratio was 1.95:1) that has been dissolved in 500 g of neral (the molar ratio of neral/geranial double bond isomers=99:1) from Example 3 having a hydroxyl value of 1 mgKOH/g and an iron content of 60 ppm by stirring in advance for 3 hours at 60° C. and at 5 MPa 1:1 (volume/volume) CO/H$_2$ pressure (the molar ratio of the substrate/catalyst (based on transition metals in catalyst) =3984), then the gas mixture in the autoclave was adjusted to hydrogen gas (8 MPa) containing 10000 ppm carbon monoxide, and the temperature was adjusted to 60° C. In the autoclave 2 in series with the autoclave 1, a gas mixture of hydrogen gas (8 MPa) containing 1000 ppm carbon monoxide and a temperature of 80° C. were set.

The feed of neral having a hydroxyl value of 1 mgKOH/g and an iron content of 60 ppm (the molar ratio of neral/geranial bond isomers=99:1) was adjusted to 70 g/h. After the neral passed through the autoclave 1 and the autoclave 2 connected in series in turn, the neral entered a distillation kettle, and the fraction containing the product was continuously distilled out at an absolute pressure of 1 KPa and at a rate of 70 g/h. 243600 g of R-citronellal whose optical purity was 80 ee % was obtained during 145 days of production.

The turnover number based on the whole reaction of R-citronellal with Rh(CO)$_2$acac was 1941215.

Example 10 (Preparation of R-Citronellal)

Under an argon gas atmosphere, 7.5 mg of Rh(CO)$_2$acac and 18.6 mg of (R,R)-chiraphos (compound of Formula (V)) (the molar ratio was 0.66:1) were dissolved in 441.8 g of neral from Example 4 having a hydroxyl value of 10 mgKOH/g and an iron content of 50 ppm (the molar ratio of neral/geranial double bond isomers=99:1; the molar ratio of the substrate/catalyst (based on the transition metal in the catalyst)=100000), and then transferred to a 1000 mL autoclave that had been purged three times in advance with a mixture of carbon monoxide and hydrogen gas (1:1 volume/volume). The mixture was stirred for 3 hours at a 1:1 (volume/volume) CO/H$_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 50° C. and reacted for 15 hours, by using gas chromatography, the conversion rate was determined to be 99.2%, and the yield of R-citronellal with an optical purity of 87 ee % was determined to be 98.2%.

The turnover number based on the whole reaction of R-citronellal with Rh(CO)$_2$acac was 98186.

Example 11 (Preparation of R-Citronellal)

Under an argon gas atmosphere, 7.5 mg of Rh(CO)$_2$acac and 18.6 mg of (S,S)-chiraphos (the molar ratio was 0.66:1) were dissolved in 441.8 g of geranial from Example 5 having a hydroxyl value of 8 mgKOH/g and an iron content of 10 ppm (the molar ratio of neral/geranial double bond isomers=99:1; the molar ratio of the substrate/catalyst (based on the transition metal in the catalyst)=100000), and then transferred to a 1000 mL autoclave that had been purged three times in advance with a mixture of carbon monoxide and hydrogen gas (1:1 volume/volume). The mixture was stirred for 3 hours at a 1:1 (volume/volume) CO/H$_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 50° C. and reacted for 15 hours, by using gas chromatography, the conversion rate was determined to be 99.9%, and the yield of R-citronellal with an optical purity of 88 ee % was determined to be 99%.

After the product was distilled, 441.8 g of geranial having a hydroxyl value of 8 mgKOH/g and an iron content of 10 ppm (the mole ratio of geranial/neral double bond isomer=99:1) were added and stirred in an autoclave at 5 MPa synthesis gas (H$_2$/CO=1:1, volume/volume) and at 60° C. for 6 hours. The reaction pressure was adjusted to 8 MPa by injecting hydrogen gas containing 1000 ppm carbon monoxide. To reduce the CO partial pressure, the pressure was reduced to 0.5 MPa three times and restored to 5 MPa three times by injecting hydrogen gas containing 1000 ppm carbon monoxide. After the mixture was heated up to 80° C. and reacted for 24 hours, by using gas chromatography, the conversion rate was determined to be 99.9%, the optical purity was determined to be 86 ee %, and the yield of R-citronellal was determined to be 99%.

After the product was distilled again, 441.8 g of geranial having a hydroxyl value of 8 mgKOH/g and an iron content of 10 ppm (the mole ratio of geranial/neral double bond isomer=99:1) were added and stirred in an autoclave at 5 MPa synthesis gas (H$_2$/CO=1:1, volume/volume) and at 60° C. for 6 hours. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 45° C. and reacted for 24 hours, by using gas chromatography, the conversion rate was determined to be 99.9%, the optical purity was determined to be 91 ee %, and the yield of R-citronellal was determined to be 99%.

The turnover number based on the whole reaction of R-citronellal with Rh(CO)$_2$acac was 297000.

Example 12 (Preparation of R-Citronellal)

For an autoclave 1 and an autoclave 2 connected in series, in the autoclave 1 was introduced a mixture of 213 mg of Rh(CO)$_2$acac and 600 mg of (R,R)-chiraphos (compound of Formula (V)) (the molar ratio was 0.59:1) that has been dissolved in 500 g of neral (the molar ratio of neral/geranial double bond isomers=99:1) from Example 6 having a hydroxyl value of 8 mgKOH/g and an iron content of 1 ppm by stirring in advance for 3 hours at 60° C. and at 5 MPa 1:1 (volume/volume) CO/H$_2$ pressure (the molar ratio of the substrate/catalyst (based on transition metals in catalyst) =3984), then the gas mixture in the autoclave was adjusted to hydrogen gas (8 MPa) containing 10000 ppm carbon monoxide, and the temperature was adjusted to 60° C. In the autoclave 2 in series, a gas mixture of hydrogen gas (8 MPa) containing 1000 ppm carbon monoxide and a temperature of 80° C. were set.

The feed of neral having a hydroxyl value of 8 mgKOH/g and an iron content of 1 ppm (the molar ratio of neral/geranial bond isomers=99:1) was adjusted to 70 g/h. After the neral passed through the autoclave 1 and the autoclave 2 in series in turn, the neral entered a distillation kettle, and the fraction containing the product was continuously distilled out at an absolute pressure of 1 KPa and at a rate of 70 g/h. 236292 g of R-citronellal whose optical purity was 91 ee % was obtained during 145 days of production.

The turnover number based on the whole reaction of R-citronellal with $Rh(CO)_2acac$ was 1882979.

Example 13 (Preparation of R-Citronellal)

Under an argon gas atmosphere, 3.75 mg of $Rh(CO)_2acac$ and 9.3 mg of (R,R)-chiraphos (compound of Formula (V)) (the molar ratio was 0.66:1) were dissolved in 441.8 g of neral having a hydroxyl value of 6 mgKOH/g and an iron content of 50 ppm (the molar ratio of neral/geranial double bond isomers=99:1; the molar ratio of the substrate/catalyst (based on the transition metal in the catalyst)=200000), and then transferred to a 1000 mL autoclave that had been purged three times in advance with a mixture of carbon monoxide and hydrogen gas (1:1 volume/volume). The mixture was stirred for 3 hours at a 1:1 (volume/volume) $CO/H_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 50° C. and reacted for 15 hours, by using gas chromatography, the conversion rate was determined to be 91.8%, the optical purity was determined to be 87 ee %, and the yield of R-citronellal was determined to be 90.6%.

The turnover number based on the whole reaction of R-citronellal with $Rh(CO)_2acac$ was 181175.

Example 14 (Preparation of R-Citronellal)

Under an argon gas atmosphere, 3.75 mg of $Rh(CO)_2acac$ and 9.3 mg of (R,R)-chiraphos (compound of Formula (V)) (the molar ratio was 0.66:1) were dissolved in 441.8 g of neral having a hydroxyl value of 1 mgKOH/g and an iron content of 10 ppm (the molar ratio of neral/geranial double bond isomers=99:1; the molar ratio of the substrate/catalyst (based on the transition metal in the catalyst)=200000), and then transferred to a 1000 mL autoclave that had been purged three times in advance with a mixture of carbon monoxide and hydrogen gas (1:1 volume/volume). The mixture was stirred for 3 hours at a 1:1 (volume/volume) $CO/H_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 50° C. and reacted for 15 hours, by using gas chromatography, the conversion rate was determined to be 91.9%, the optical purity was determined to be 87 ee %, and the yield of R-citronellal was determined to be 90.7%.

The turnover number based on the whole reaction of R-citronellal with $Rh(CO)_2acac$ was 181375.

Examples 15-18 (Preparation of R-Citronellal)

Under an argon gas atmosphere, 0.015 mmol of a transition metal compound (see Table 1 below) and 0.03 mmol of an optically active ligand containing two phosphorus atoms (see "Ligand" in Table 1 below) were dissolved in 456 g of neral having a hydroxyl value of 6 mgKOH/g and an iron content of 50 ppm (the molar ratio of neral/geranial double bond isomers=99:1; the molar ratio of the substrate/catalyst (based on the transition metal in the catalyst)=200000), and then transferred to a 1000 mL autoclave that had been purged three times in advance with a mixture of carbon monoxide and hydrogen gas (1:1 volume/volume). The mixture was stirred for 3 hours at a 1:1 (volume/volume) $CO/H_2$ pressure of 0.8 MPa and at 60° C. and then cooled to room temperature. The reaction pressure was adjusted to certain pressure (see "Pressure" in Table 1 below) by injecting hydrogen gas containing carbon monoxide of a certain concentration (see "CO concentration" in Table 1 below). To reduce the CO partial pressure, the pressure was reduced to 0.8 MPa three times and restored to certain pressure (see "Pressure" in Table 1 below) three times by injecting hydrogen gas containing carbon monoxide of a certain concentration (see "CO concentration" in Table 1 below). The mixture was heated up to a certain temperature (see "Temperature" in Table 1 below), and after the reaction was completed, the yield of R-citronellal was determined by gas chromatography, and the turnover number of the whole reaction was calculated based on the molar amount of produced R-citronellal and the molar amount of the used transition metal compound. The specific process parameters and experimental results are listed in Table 1 below:

TABLE 1

| Example | Transition metal compound | Ligand | CO concentration(ppm) | Pressure (MPa) | Temperature (° C.) | Yield (%) | Turnover number |
|---|---|---|---|---|---|---|---|
| 15 | $[Rh(cod)OH]_2$ | Formula (V) | 100 | 8 | 120 | 75 | 150000 |
| 16 | $[Rh(cod)OMe]_2$ | Formula (VI) | 1000 | 6 | 90 | 68 | 136000 |
| 17 | $Rh_4(CO)_{12}$ | Formula (VII) | 10000 | 5 | 55 | 92 | 184000 |
| 18 | $Rh_6(CO)_{16}$ | Formula (VIII) | 1000 | 5 | 25 | 91 | 182000 |

Comparative Example 1

Under an argon gas atmosphere, 7.5 mg of $Rh(CO)_2acac$ and 18.6 mg of (R,R)-chiraphos (compound of Formula (V)) were dissolved in 441.8 g of neral having a hydroxyl value of 10 mgKOH/g and an iron content of 70 ppm (the molar ratio of neral/geranial double bond isomers=99:1; the molar ratio of the substrate/catalyst=100000), and then transferred to a 1000 mL autoclave that had been purged three times in advance with a mixture of carbon monoxide and hydrogen gas (1:1 volume/volume). The mixture was stirred for 3 hours at a 1:1 (volume/volume) $CO/H_2$ pressure of 0.8 MPa and at 60° C. and then cooled to room temperature. The reaction pressure was adjusted to 8 MPa by injecting hydrogen gas containing 1000 ppm carbon monoxide. To reduce the CO partial pressure, the pressure was reduced to 0.8 MPa three times and restored to 8 MPa three times by injecting hydrogen gas containing 1000 ppm carbon monoxide. After the mixture was heated up to 60° C. and reacted for 18 hours, by using gas chromatography, the conversion rate was determined to be 12%, and the selectivity of R-citronellal with an optical purity of 80 ee % was 92%.

The turnover number based on the whole reaction of R-citronellal with $Rh(CO)_2acac$ was 11038.

Those skilled in the art will appreciate that some modifications or adaptations may be made to the present disclosure based on the teachings of the description. These modifications or adaptations should fall within the scope of the present disclosure as defined by the claims.

What is claimed is:

1. A preparation method for optically active citronellal, wherein a substrate is subjected to an asymmetric hydrogenation reaction in the presence of a transition metal catalyst to generate the optically active citronellal, the transition metal catalyst is obtained by reacting a transition metal compound with an optically active ligand containing two phosphorus atoms, and the substrate is selected from one or two of neral of Formula (I) and geranial of Formula (II), wherein the substrate for the asymmetric hydrogenation reaction is controlled to have a hydroxyl value less than or equal to 6 mgKOH/g and/or an iron content less than or equal to 50 ppm:

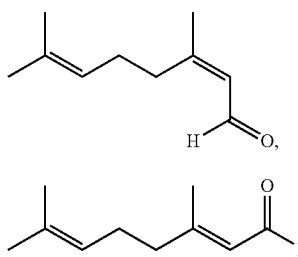

Formula (I)

Formula (II)

2. The preparation method according to claim 1, wherein the optically active citronellal is optically active R-citronellal of Formula (III):

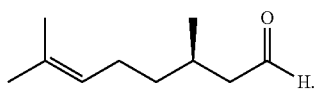

Formula (III)

3. The preparation method according to claim 1, wherein the optically active ligand containing two phosphorus atoms is a ligand of general formula (IV):

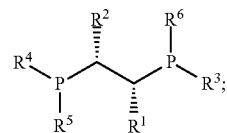

Formula (IV)

wherein,
$R^1$ and $R^2$ are each independently a hydrogen atom or unbranched, branched or cyclic alkyl having 1-20 carbon atoms, and optionally carry one or more ethylenic double bonds and/or optionally carry one or more identical or different substituents selected from the group consisting of halogen, $C_6$-$C_{10}$ aryl and $C_3$-$C_9$ heteroaryl; or $R^1$ and $R^2$ together may form one or more 4- to 20-membered rings;
$R^3$, $R^4$, $R^5$ and $R^6$ are identically or differently $C_6$-$C_{10}$ aryl and each optionally carry one or more substituents selected from the group consisting of $C_1$-$C_4$ alkyl, $C_6$-$C_{10}$ aryl, $C_1$-$C_4$ alkoxy and amino.

4. The preparation method according to claim 3, wherein the optically active ligand containing two phosphorus atoms has a structural formula (V), (VI), (VII) or (VIII) or is any of enantiomers of structural formulas (V)-(VIII):

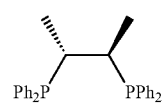

Formula (V)

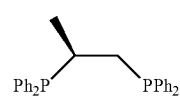

Formula (VI)

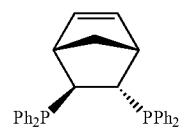

Formula (VII)

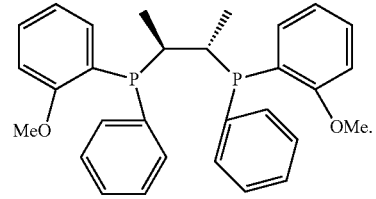

Formula (VIII)

5. The preparation method according to claim 1, wherein the transition metal compound is soluble in a reaction mixture for the asymmetric hydrogenation reaction; the transition metal compound is a compound of a metal of Group VIII of the Periodic Table of Elements.

6. The preparation method according to claim 1, wherein the molar ratio of transition metal atoms in the transition metal compound to the optically active ligand is (0.5-10):1.

7. The preparation method according to claim 1, comprising the following steps:
dissolving the transition metal compound and the optically active ligand containing two phosphorus atoms in the substrate under an inert gas atmosphere, to obtain a mixed material containing the catalyst; before carrying out the asymmetric hydrogenation reaction, stirring the mixed material at 40° C.-80° C. for 1-6 hours under the condition that the volume ratio of $CO/H_2$ is ½-¾ and the pressure is 0.5-5 MPa, and then cooling the mixed material, to obtain a mixed material containing a pretreated catalyst;

subjecting the mixed material containing the pretreated catalyst to a reaction under reaction conditions required for carrying out the asymmetric hydrogenation reaction, to obtain the optically active citronellal.

8. The preparation method according to claim 1, wherein the asymmetric hydrogenation reaction is carried out in the presence of hydrogen gas containing 100-10000 ppm carbon monoxide.

9. The preparation method according to claim 1, wherein the asymmetric hydrogenation reaction is carried out at an absolute pressure of 0.1-10 MPa.

10. The preparation method according to claim 1, wherein the reaction temperature of the asymmetric hydrogenation reaction is 25° C. -120° C.

11. The preparation method according to claim 1, wherein the turnover number of the transition metal catalyst is greater than 50000.

12. The preparation method according to claim 1, wherein based on the amount of the substrate, the amount of the transition metal compound is 0.0001 mol % to 0.1 mol % based on the molar amount of transition metal atoms.

13. The preparation method according to claim 1, wherein the substrate for the asymmetric hydrogenation reaction is previously subjected to a rectification treatment to enable the hydroxyl value to be less than or equal to 6 mgKOH/g and/or the iron content to be less than or equal to 50 ppm in the substrate.

14. The preparation method according to claim 3, wherein $R^1$ and $R^2$ together form one or more 4- to 20-membered rings, and wherein the ring contains unsaturated double bonds, and ring-forming atoms on the ring are C atoms.

15. The preparation method according to claim 5, wherein the transition metal compound is one or more of compounds of Ru, Rh, Pd, Ir and Pt.

16. The preparation method according to claim 15, wherein the transition metal compound is a compound of Rh.

17. The preparation method according to claim 6, wherein the molar ratio of transition metal atoms in the transition metal compound to the optically active ligand is (0.5-2):1.

18. The preparation method according to claim 9, wherein the asymmetric hydrogenation reaction is carried out at an absolute pressure of 5-8 MPa.

19. The preparation method according to claim 10, wherein the reaction temperature of the asymmetric hydrogenation reaction is 50° C.-90° C.

* * * * *